(12) United States Patent
Malthe-Sørenssen et al.

(10) Patent No.: US 6,232,499 B1
(45) Date of Patent: May 15, 2001

(54) PROCESS FOR THE PRODUCTION OF IODINATED ORGANIC X-RAY CONTRAST AGENTS

(75) Inventors: Dick Malthe-Sørenssen; Anne Cathrine Schelver Hyni; Arne Aabye; Hans René Bjørsvik; Geir Brekke; Carl Einar Sjøgren, all of Oslo (NO)

(73) Assignee: Nycomed Imaging AS, Oslo (NO)

( * ) Notice: Subject to any disclaimer, the term of this patent is extended or adjusted under 35 U.S.C. 154(b) by 0 days.

(21) Appl. No.: 09/318,804

(22) Filed: May 26, 1999

Related U.S. Application Data

(63) Continuation of application No. PCT/GB97/03205, filed on Nov. 21, 1997.
(60) Provisional application No. 60/046,646, filed on May 16, 1997.

(30) Foreign Application Priority Data

Nov. 26, 1996 (GB) .................................................. 9624612

(51) Int. Cl.⁷ .......................... C07C 233/64; A61K 49/04
(52) U.S. Cl. ........................................ 564/153; 424/9.454
(58) Field of Search ........................... 424/9.454; 564/153

(56) References Cited

U.S. PATENT DOCUMENTS

| | | |
|---|---|---|
| 4,001,323 | 1/1977 | Felder et al. . |
| 4,640,833 * | 2/1987 | Tamborski et al. . |
| 5,191,119 | 3/1993 | Sovak et al. . |
| 5,686,061 | 11/1997 | Chun et al. . |

FOREIGN PATENT DOCUMENTS

| | | |
|---|---|---|
| 0 120 583 | 10/1984 | (EP) . |
| WO 97/27172 | 7/1997 | (WO) . |

OTHER PUBLICATIONS

Priebe et al., ACTA Radiol Suppl, 399 pp. 21–31 (1995).
Felder et al., Analytical Profiles of Drug Substances, vol. 17, 115–154 (1988).
Schlotter, N. E., Polym. Prepr., 32(3), 681–2, 1991.*

* cited by examiner

*Primary Examiner*—Shailendra Kumar
(74) *Attorney, Agent, or Firm*—Bacon & Thomas

(57) ABSTRACT

The present invention provides a process for the production of an organic iodinated X-ray contract agent, characterized in that process control comprises vibrational (e.g., infrared, Raman or preferably near-infrared) spectroscopic monitoring of the reaction mixture in at least one of the process steps, preferably one of the final reaction steps.

15 Claims, 5 Drawing Sheets

PROCESS FOR THE PRODUCTION OF IODINATED ORGANIC X-RAY CONTRAST AGENTS

This application is a continuation of pending international application number PCT/GB97/03205 filed Nov. 21, 1997 (of which the entire disclosure of the pending, prior application is hereby incorporated by reference), which itself is a continuation-in-part of U.S. provisional application Ser. No. 60/046,646 filed May 16, 1997.

This invention relates to improvements in and relating to the manufacture of iodinated organic X-ray contrast agents.

For many years, the X-ray contrast media market has been dominated by the inorganic barium compounds used for imaging the gastrointestinal tract and the parenterally-administered organic iodinated compounds used for imaging elsewhere, in particular the circulatory system. These iodinated compounds, such as iohexol, iopentol, iodixanol, ioversol, iopamidol, ioxaglate, metrizoate, metrizamide, etc., are manufactured and sold as pharmaceuticals and as with the commercial manufacture of any pharmaceutical compound it is important to optimize their efficiency of manufacture (eg. to maximize yield and purity while minimizing demand on equipment, materials and time).

As pharmaceuticals however, the manufacture of iodinated X-ray contrast agents is dominated by the requirement for product purity and accordingly most process steps are monitored using the "gold standard" of HPLC which gives a clear and unmistakeable indication of the presence and likely identity of by-products and residual reagents in any reaction mixture.

HPLC however is a relatively slow technique taking perhaps several hours from sampling to completion of data analysis and offers little freedom to the process operators for real-time feedback control of process performance.

The present inventors have now realised that more rapid, and indeed on-line monitoring, of the processes for the production of iodinated X-ray contrast agents can surprisingly be achieved using vibrational (eg. near infrared (NIR), infrared or Raman) spectroscopy. Such an on-line monitoring system allows a more rapid response in process control, eg. in terms of changing process conditions such as temperature, pressure and pH, controlling addition of reagents, or terminating reactions at the optimal point. That such spectroscopic techniques can be used for this purpose is doubly surprising. Firstly, it is surprising that a spectrum of a complex reaction mixture can be used as such to reliably predict the amount of single species, without first requiring the use of separation techniques such as chromatography, even when product purity is of paramount concern such as is the case with drug substances. Secondly, vibrational spectrometry has for many years been viewed as an academic tool, with little or no relevance for process monitoring and complex reaction mixtures. Contrary to what was believed, it is now surprisingly found that vibrational spectroscopic techniques (eg. infrared and NIR spectrometry) are applicable even to reaction mixtures with high aqueous contents. With Raman spectroscopy, high water contents of the solvent are not problematic. Raman spectrometry, moreover, is particularly sensitive to detection of molecular species with large numbers of polarisable electrons, such as iodinated X-ray contrast agents.

NIR spectroscopy has previously been used for monitoring of hydrocarbons (see for example WO 91/15762, U.S. Pat. No. 4,963,745, DD-272129 and WO 89/06244) but has not previously been suggested as being suitable for monitoring production of contrast agents, especially X-ray and MRI contrast agents.

Thus viewed from one aspect, the present invention provides a process for the production of an organic iodinated X-ray contrast agent, characterized in that process control comprises vibrational (eg. infrared, Raman or preferably near-infrared) spectroscopic monitoring of the reaction mixture in at least one of the process steps, preferably one of the final reaction steps.

Monitoring using vibrational spectroscopic techniques according to the invention will typically involve deriving characteristic data values from the detected spectra, comparison of such characteristic values with calibration data and modification of process parameters based on the outcome of the comparison. All these steps may, and preferably will, be automated with the process of the invention being operated under computer control.

The manufacturing of contrast agents, eg. organic iodinated X-ray contrast agents, includes production of the chemical drug substance (the "primary production"), followed by formulation to the drug product (the "secondary production"). The drug substance is usually made and purified in a multi-step chemical synthesis and the monitoring according to the invention may take place in one, some or all of these multiple steps, and particularly conveniently comprises monitoring of the reactor contents in at least one, and preferably two to six, of the final reaction steps. For the purposes of the present invention a reaction step is defined as a process which involves converting one isolatable and purifiable compound into another or the transformation of a compound from one form to another (eg. a precipitation or crystallization or a phase change or the formation of an amorphous form of a product) and/or an essentially mechanical step such as the cleaning of equipment. Such compounds will either be reagents (starting materials not manufactured by the process operator), intermediates, or the final drug substance.

The vibrational spectra of crystalline iodinated organic X-ray contrast agents are usually sufficiently different from those of the corresponding amorphous materials or indeed from those of the same agents in different crystalline forms as to allow unambiguous identification of the crystalline form being monitored. Raman spectra show the same level of detail as infrared spectra with respect to band shifts and splittings caused by different solid (polymorphic) forms of a substance, but Raman spectrometers are more conveniently coupled on-line, eg. to a reaction vessel in which an iodinated X-ray contrast agent is precipitated from a solution. The grain size of the resulting solid will also affect the appearance of the infrared, NIR and Raman spectra, so that other physical characteristics of the solid could also be inferred from the spectra.

In one embodiment, the present invention therefore involves a process for the production of an iodinated X-ray contrast agent, involving an on-line quantitative monitoring of physical characteristics (eg. crystal size, crystal type, etc.) of the desired product. This monitoring may be done on-line during precipitation of the solid substance, by multivariate calibration and/or classification and Raman spectrometry coupled to the reaction vessel by means of optical fibres and a suitable optical window through which the exciting laser light is transmitted and the resulting Raman scattering is collected and transmitted back to the spectrometer. Alternatively, commercially available infrared waveguides and optical windows may be used to connect an infrared (FT-IR) spectrometer to the reaction vessel, or a NIR spectrometer may be connected using optical fibres, and the spectral data may be collected and the physical characteristics of the precipitate may be predicted from a suitable multivariate calibration and/or classification model, eg. based on reference spectra of pure polymorphs or mixtures thereof.

In the process of the invention, vibrational spectroscopic data (eg. NIR spectroscopic data) are collected for the reaction mixture, either by in-situ measurement, on-line sampling (eg. drawing off a sample through a line delivering the sample to the spectroscopic apparatus) or off-line sampling (eg. drawing off of a discrete sample and placing some or all of that sample in the spectroscopic apparatus). The sample monitored may thus be in or taken from a reaction vessel or a duct connecting reaction vessels. All of these data collection steps may be effected automatically, eg. under computer control; however of these, in situ measurement and on-line sampling are preferred since the delay before spectroscopic measurement can be minimized.

The spectroscopic data generated is conveniently subject to an automated calculation procedure, eg. based on a previously established multivariate calibration, allowing almost instantaneous feedback to the process control system (which will conveniently be computer controlled). Thus spectroscopic analysis gives the possibility to make adjustments to process parameters or to take actions (eg. addition of reagents, termination of reaction etc.) almost instantly so as to maintain or achieve optimal selectivity in the synthesis.

The calibration referred to above will conveniently be done with reference to a high accuracy analysis system appropriate to the system and property under investigation, eg. HPLC or TLC. Thus a synthetic or other process step may be run with samples being taken repeatedly throughout the progress of the reaction, and those samples being subject to both spectroscopic (eg. NIR) and HPLC analysis. Multivariate analysis of the vibrational (eg. NIR) spectra may then be performed to identify the spectral status that corresponds uniquely to the HPLC results for the optimum stage at which to effect a process change (eg. addition of further reagent, termination of reaction, change to different pH, temperature or pressure, etc.) and similarly the effects of undesired process changes (eg. incorrect pH, temperature or pressure, or inadequate or excess reagent) on the spectrum may be determined so that, where these effects are detected, the appropriate corrective action may be taken. In other words, from a set of calibration samples analysed by both the selected vibrational spectroscopic technique used in the process of the invention (eg. NIR) and the reference method (eg. HPLC) a calibration model may be constructed from which the characteristics of unknown samples can be predicted. In subsequent operation of the process of the invention the results from spectroscopic analysis are obtained within seconds and appropriate action to adjust reaction conditions (eg. to stop conversion of product to by-product or to terminate the reaction at the most efficient point) may be taken with less delay than is possible using the conventional chromatographic methods.

Multivariate analysis of spectra to generate the calibration model may be performed using conventional techniques, eg. as discussed in "Multivariate Calibration" by Martens and Nes, John Wiley & Sons, 1991.

While the invention is primarily concerned with preparation of organic iodinated X-ray contrast agents, and in particular non-ionic X-ray contrast agents (eg. iohexol, iopentol, iodixanol, iopamidol and ioversol), it is also applicable to organic contrast agents as a whole and particularly to process steps in which the reaction mixture is slightly aqueous (eg. up to 5%, especially up to 2% and more particularly up to 1% by weight) either due to inclusion of water in the starting materials or due to generation of water during the reaction. When Raman spectroscopy is used, the reaction mixtures may even be significantly more aqueous, eg. liquid phases may contain up to 50% or even 70% by weight water, for example in cases where water is present as a solvent or co-solvent or where it is added as a non-solvent (for example to precipitate out a dissolved compound). In on-line monitoring of rinse water, etc, as is described in Example 2 below, the water content of the system under study may be still higher.

X-ray contrast agents and intermediates in the syntheses of such agents are often polyiodinated aromatic amides with several hydroxylic groups attached. The intermediates, some of which lack iodine substituents, frequently possess primary, secondary or tertiary amino groups. The process of the invention will however be described by way of example with reference to the production of iodixanol (1,3-bis(acetamido)-N,N'-bis[3,5-bis(2,3-dihydroxypropylaminocarbonyl)-2,4,6-triiodophenyl]-2-hydroxypropane). This contrast agent has the following chemical structure:

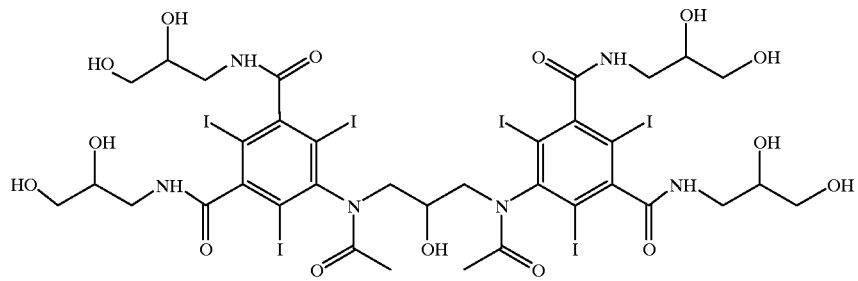

The process step monitored using the process of the invention will generally take place in the gas phase or in the liquid phase. Particularly conveniently it will involve a liquid phase containing a solvent or solvent mixture and optionally anti-solvents. The solvent, co-solvents or anti-solvents may be any material capable of functioning as solvents or anti-solvents, but preferably will be materials with as few peaks as possible in the spectra being studied close to or overlapping with the peaks of the compounds of interest. Examples include water, aliphatic hydrocarbons, aromatic hydrocarbons, halogenated hydrocarbons, alcohols, polyols, ketones, esters, ethers, nitrites, DMSO, DMF, etc., eg. water, $C_{1-4}$ alkanols, $C_{2-6}$ alkoxyalkanols, $C_{2-6}$ linear or cyclic ethers, $C_{3-6}$ ketones, $C_{2-6}$ esters, $C_{4-10}$ hydrocarbons, $C_{1-4}$ haloalkanes, etc.

As mentioned above, the manufacturing processes of the contrast agents usually constitute several chemical transformations, with a number of intermediates involved.

Vibrational spectra (eg. near infrared spectra) of mixtures of contrast agents and/or their intermediates can easily be collected by a spectrophotometer (eg. a near infrared spectrophotometer) and a probe connected to the instrument by one or more optical fibres. For calibration, several scans should be collected of each sample, and the reaction solvent may appropriately be used as a reference.

The building of the calibration model from the calibration sample set can easily be performed by techniques known to those skilled in the art. Standard methods for a multivariate calibration may be applied. The parameters of interest must be determined by a reference method during the building of the calibration method. The accuracy of the predicted values from the calibration model thus cannot be better than what is obtained with the reference method of analysis.

Once the calibration model is built up, an unknown sample can be measured by the appropriate spectrophotometer, and the resulting spectrum can be correlated with the calibration data. A calculation of predicted values of the parameters of interest can be performed by a computer within a few seconds, and the analytical results can be printed out or displayed on a computer screen, or it may if desired be fed directly into a control algorithm, which in turn initializes the correct action in the regulation of the process.

The invention will now be illustrated by reference to the following non-limiting Examples and the accompanying drawings, in which.

EXAMPLE 1

Figure 1:
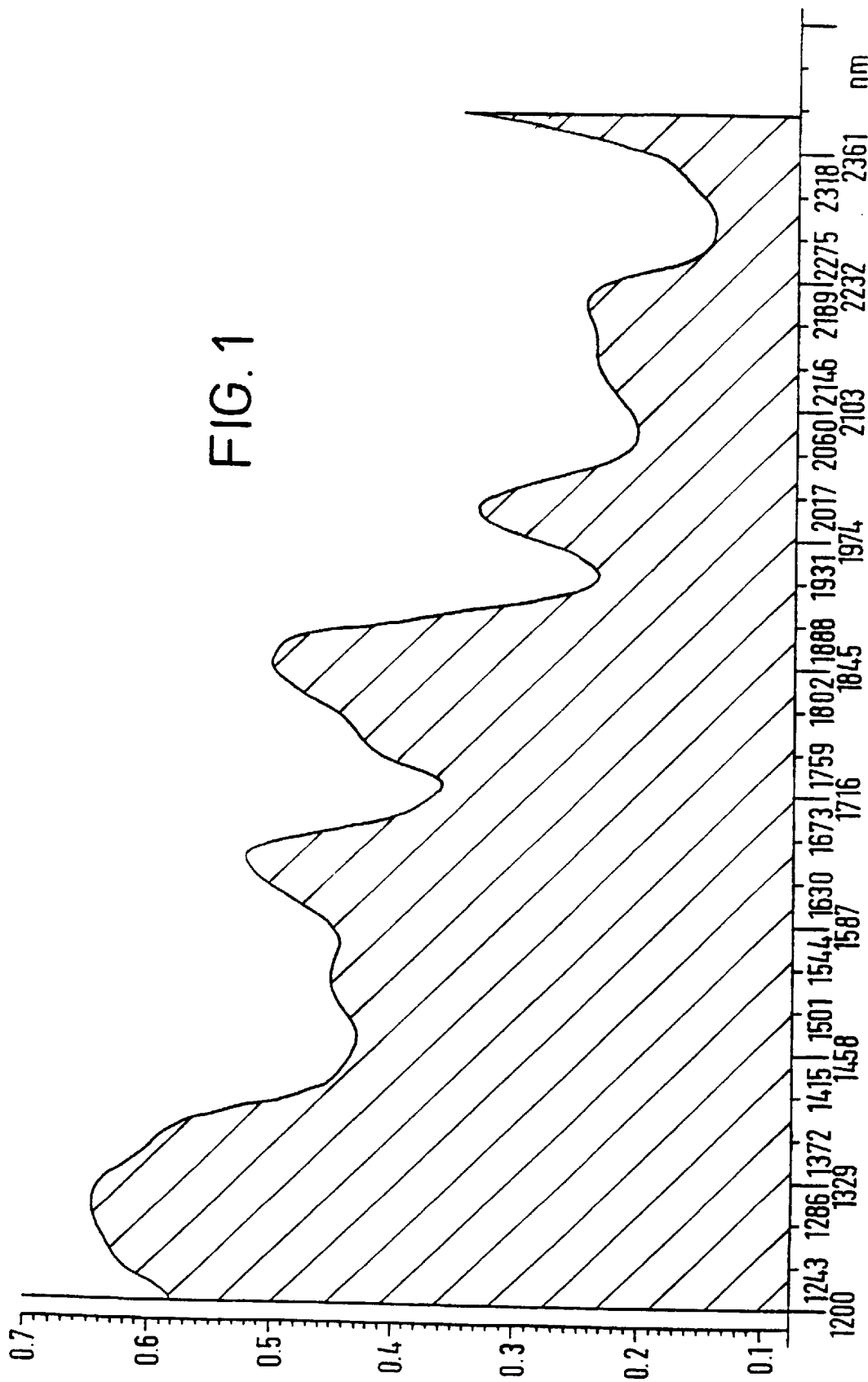
FIG. 1 is a plot of an NIR spectrum for a reaction mixture in the synthesis of iodixanol.

Synthesis of Iodixanol from 5-Acetamido-N,N'-Bis(2,3-Dihydroxypropyl)-2,4,6-Triiodo-Isophtalamide All experiments were carried out in a 1 L jacketed glass reactor equipped with a stirrer and a water bath. NIR transflectance spectra were collected with a Quantum 1200 Plus NIR analyzer (LT Industries Inc.) in the spectral region from 1200 nm to 2400 nm with fibre optics and a Bubble Shedding probe with a pathlength of 2 mm. 90 scans were collected for each spectrum, and air was used as the background. Two spectra were collected of each sample. HPLC (reversed phase, water/acetonitrile) was used as the reference method, with one or three parallels of each sample.

The following procedure was used in all the three experiments: 2-methoxyethanol (300 ml) and sodium hydroxide (20 g) was added to the reactor at 50° C., and 5-acetamido-N,N'-bis(2,3-dihydroxypropyl)-2,4,6-triiodoisophtalamide (304 g) was added after two hours of stirring. All solids were allowed to dissolve overnight before cooling to 30° C. and adjustment to pH 12 with diluted hydrochloric acid. Epichlorohydrin (11 g) was added to the solution after further cooling to 15° C., and the reaction was allowed to proceed for 51 hours. 16–20 samples were taken during the reaction time, and quenched with hydrochloric acid before HPLC analysis. NIR spectra were simultaneously collected directly in the reaction mixture, even when precipitated material was present in the reactor.

The total amount of overalkylated substances in each sample was determined by HPLC. The overalkylated substances are a number of compounds formed by reaction with more than one equivalent of alkylating agent, and may contain more than two aromatic rings. The overalkylated substances have longer retention times than iodixanol itself on reversed phase HPLC columns. The results of the HPLC analyses are summarized in Table 1. Note that the sample times are different in each experiment.

TABLE 1

| | HPLC results | | |
|---|---|---|---|
| Experiment no. Sample no. | 1 Overalkylated substances (area %) | 2 Overalkylated substances (area %) | 3 Overalkylated substances (area %) |
| 1 | 1.9 | 0.751 | 0.717 |
| 2 | 1.8 | 0.939 | 0.741 |
| 3 | 1.8 | 1.161 | 0.760 |
| 4 | 1.7 | 1.165 | 0.780 |
| 5 | 1.8 | 1.217 | 0.753 |
| 6 | 1.8 | 1.386 | 0.803 |
| 7 | 1.7 | 1.393 | 0.818 |
| 8 | 1.5 | 1.401 | 0.831 |
| 9 | 1.6 | 1.462 | 0.860 |
| 10 | 1.6 | 1.487 | 0.842 |
| 11 | 1.6 | 1.397 | 0.859 |
| 12 | 1.6 | 1.405 | 1.165 |
| 13 | 1.6 | 1.512 | 1.127 |
| 14 | 1.6 | 1.527 | 1.166 |
| 15 | 1.6 | 1.509 | 1.178 |
| 16 | 1.6 | 1.703 | 1.210 |
| 17 | 1.6 | — | 1.200 |
| 18 | 1.6 | — | 1.217 |
| 19 | — | — | 1.220 |
| 20 | — | — | 1.256 |

Figure 2:
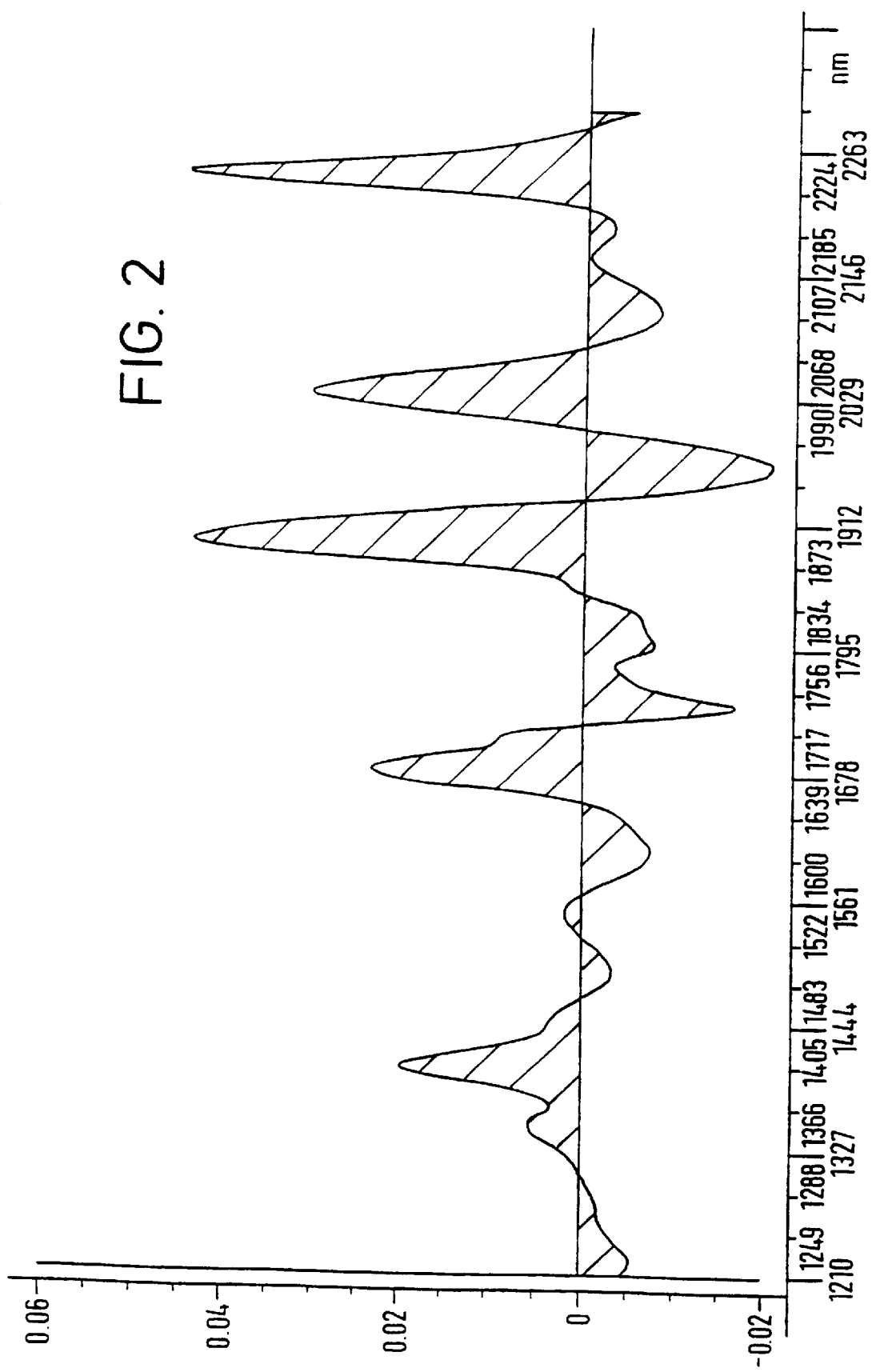
FIG. 2 is a plot of the NIR spectrum of FIG. 1 following pre-treatment.

A calibration model was built up from the sample data given in Table 1 using Unscrambler II (version 5.0), a program available from Camo (Computer-Aided Modelling A/S), Trondheim. The aim of the model was to predict the content of overalkylated substances in the reaction mixture from the corresponding NIR spectra. The raw spectra from the NIR analyzer were pretreated before being used to build the model. The preferred pretreatment of the spectra is the following:

1. Dividing by the reference spectrum of air
2. Converting from transflectance to absorbance by $\log(1/x)$
3. Area normalization to compensate for differences in absorption caused by turbid solution FIG. 1 and FIG. 2 of the accompanying drawings show an example of NIR spectrum before (FIG. 1) and after (FIG. 2) pretreatment as described above.

Figure 3:
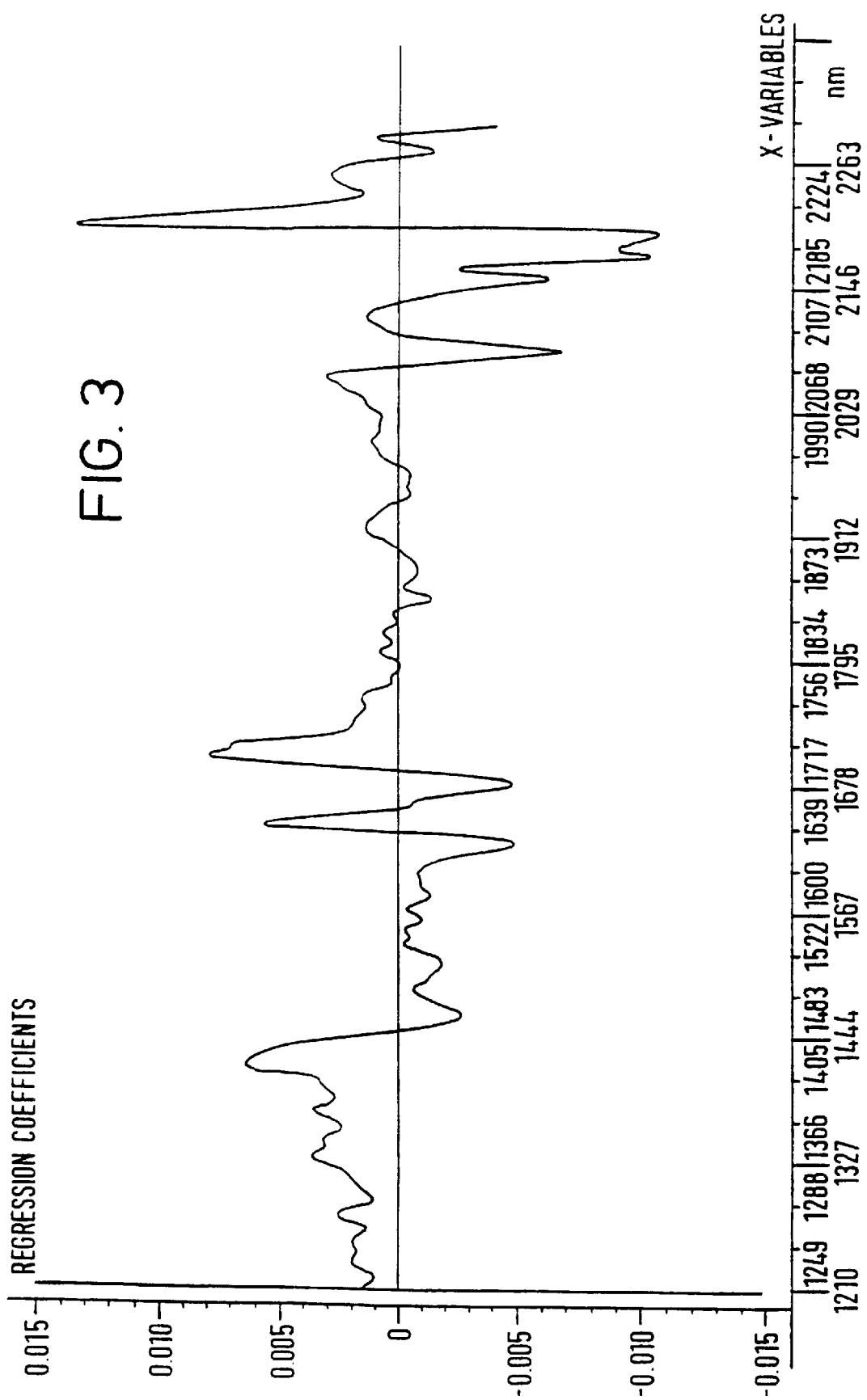
FIG. 3 is a plot of the spectral weighting for a calibration model.

Separate calibration models for each of the three experiments were made after pretreatment of the spectra as indicated above. Subsequently, the results of all the experiments were combined into one model. The different parts of each spectrum are given different weight in the calibration model, i.e. different regression coefficients. A graphical plot of the weighing in the combined model is shown in FIG. 3 of the accompanying drawings. A summary of the calibration results is given in Table 2.

TABLE 2

Calibration results. Y in the table represents the content of overalkylated substances in the samples (area %)

| Experiment | % of Y explained | Correlation | Standard error of prediction | Slope of regression line |
|---|---|---|---|---|
| 1 | 80.4 | 0.820 | 0.063 | 0.746 |
| 2 | 87.4 | 0.901 | 0.082 | 0.846 |
| 3 | 97.7 | 0.977 | 0.044 | 0.934 |
| Combined | 93.1 | 0.953 | 0.105 | 0.918 |

The figures in Table 2 indicate that, e.g., 97.7% of the variation of Y (content of overalkylated substances) can be explained by the calibration model for experiment 3. In total, the combined calibration model is able to explain 93.1% of the Y variation. The correlation between the input values (reference values determined by HPLC) and the output values (the corresponding values predicted by the model) is 0.918. A perfect correlation would be 1.000, which would mean that a perfect linearity between the NIR spectra and the Y values was observed for all the reference data.

Figure 4:
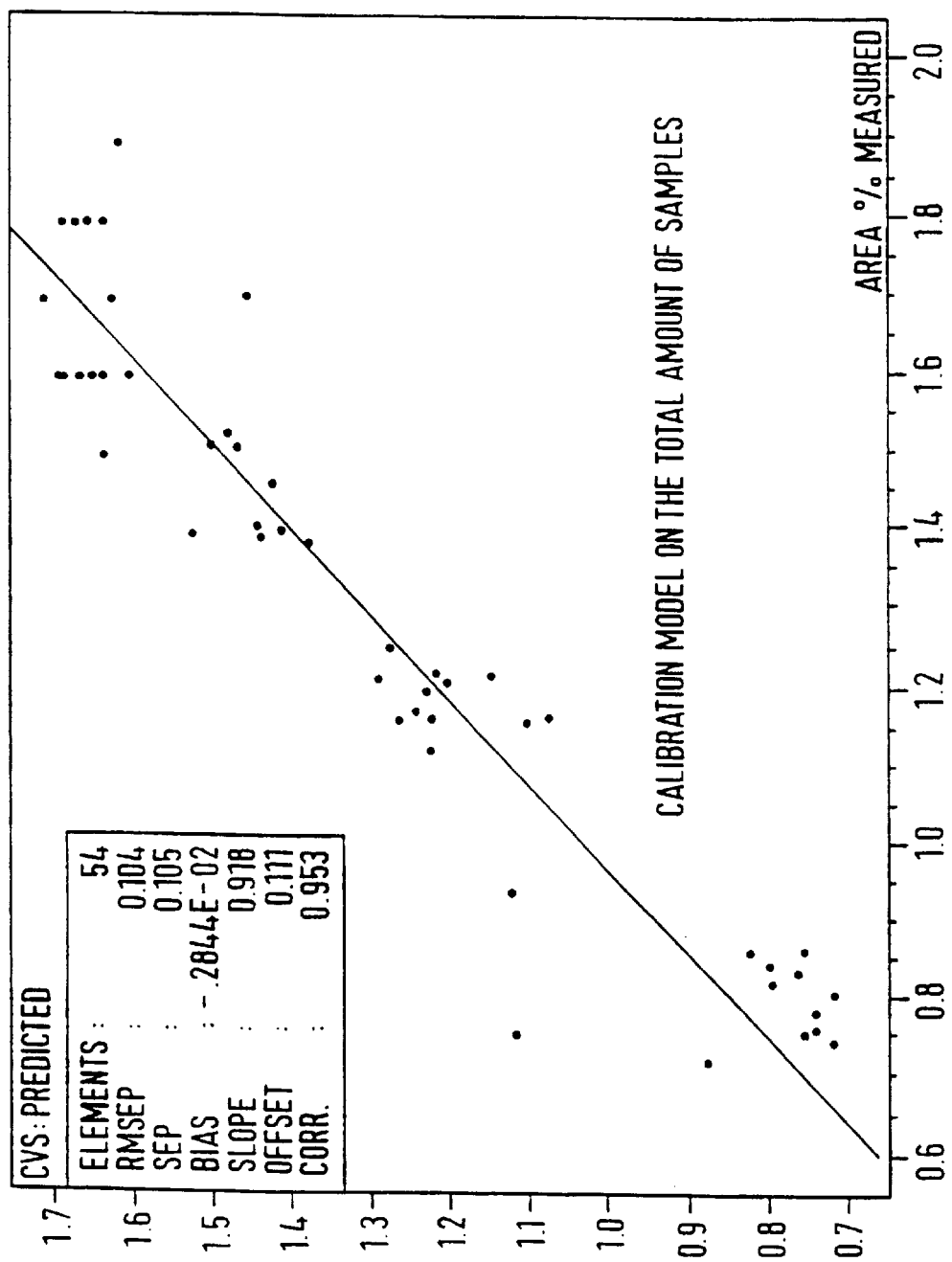
FIG. 4 is a plot comparing values indicative of the degree of overalkylation as measured and as predicted using the calibration model of FIG. 3.

A graphical presentation of the results from the combined model is given in FIG. 4 of the accompanying drawings. This is a plot of area % values for overalkylated substances as predicted (from the NIR spectra) by the combined model compared with the values determined by HPLC.

The models mentioned above were built using all the samples. To check the predictive value of the model, the data was randomly split into calibration samples and prediction samples. Three samples from experiments 1 and 2 and four samples from experiment 3, in addition to nine other samples from the combined data, were picked out to be used as prediction samples, while a calibration model was built upon the rest of the samples. This comparison of predicted and measured values gave the following results, set out in Table 3:

TABLE 3

Predicted and measured values of content of overalkylated substances (area %).

| Experiment | Prediction sample | Measured value | Predicted value | Deviation |
|---|---|---|---|---|
| 1 | 1-5 | 1.8 | 1.704 | 0.054 |
|   | 1-9 | 1.6 | 1.589 | 0.043 |
|   | 1-17 | 1.6 | 1.627 | 0.051 |
| 2 | 2-6 | 1.386 | 1.407 | 0.121 |
|   | 2-13 | 1.512 | 1.522 | 0.057 |
|   | 2-15 | 1.509 | 1.562 | 0.062 |
| 3 | 3-3 | 0.760 | 0.740 | 0.043 |
|   | 3-9 | 0.860 | 0.811 | 0.036 |
|   | 3-14 | 1.166 | 1.200 | 0.019 |
|   | 3-19 | 1.220 | 1.204 | 0.031 |
| Combined | 1-3 | 1.8 | 1.702 | 0.081 |
|   | 1-8 | 1.5 | 1.629 | 0.077 |
|   | 1-13 | 1.6 | 1.681 | 0.048 |
|   | 2-2 | 0.939 | 1.108 | 0.109 |
|   | 2-3 | 1.161 | 1.133 | 0.087 |
|   | 2-7 | 1.393 | 1.438 | 0.067 |
|   | 3-2 | 0.741 | 0.725 | 0.056 |
|   | 3-7 | 0.818 | 0.793 | 0.068 |
|   | 3-16 | 1.210 | 1.197 | 0.048 |

Figure 5:
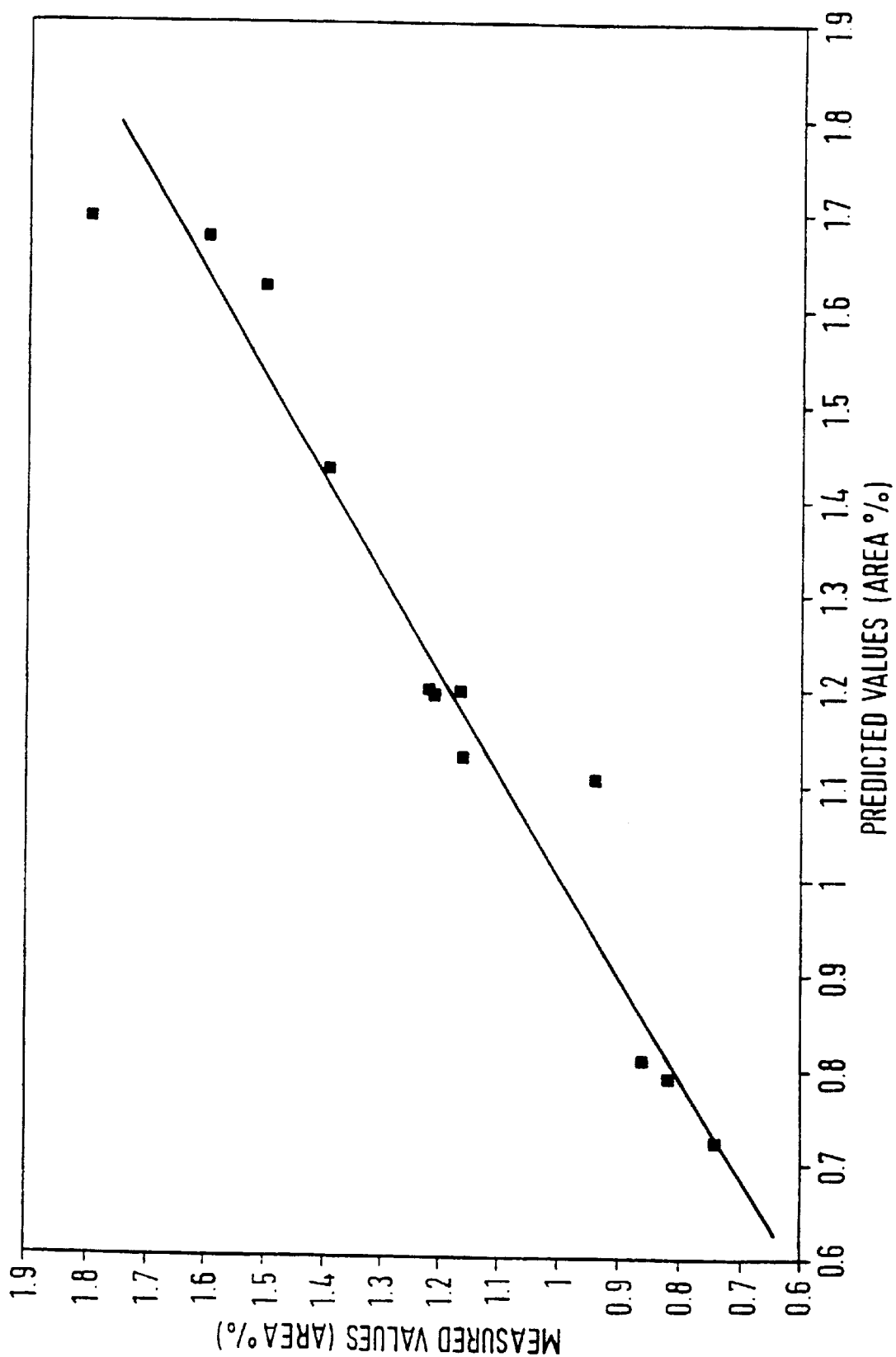
FIG. 5 is a plot comparing values indicative of the degree of overalkylation as measured and as predicted using a further calibration model.

The data set out in Table 3 is also presented graphically in FIG. 5 of the accompanying drawings.

Necessary actions during the synthesis are taken based on the content of overalkylated substances in the reaction mixture. Such actions may be, e.g. termination of the reaction by addition of hydrochloric acid when a content of overalkylated substances of 1.4% or more is detected, or alternatively addition of small amounts of hydrochloric acid to decrease pH if the content of overalkylated substances is determined to more than 0.7 % after 22 hours of reaction. The calculations reviewed in this example show that HPLC analyses can be replaced by on-line NIR analyses to determine the content of overalkylated substances sufficiently accurate for the appropriate time for the necessary actions to be taken to be identified with minimal delay.

EXAMPLE 2

Monitoring of Rinse Water and Effluent from Process Equipment used in the Production of Iodinated X-Ray Contrast Agents Solutions of iohexol with concentrations of 0.00 (distilled water), 0.25, 0.45, 0.9, 1.80 and 18.0 mg iodine/mL were prepared. Raman spectra of the samples were recorded on a Labram Raman spectrometer (Dilor, France) with an acquisition time of 300 seconds and a laser power of 40 mW (Ar laser, 514.5 nm wavelength). Spectral data comprising a very intense Raman band at ca. 170 $cm^{-1}$, which is characteristic of tri-iodinated, aromatic rings, were fed into a multivariate calibration software and the detection limit (DL) of iohexol in water was estimated from the standard error of prediction determined from a plot of predicted versus known concentration values. A standard error of prediction of 0.45 mgI/mL was obtained which yields a DL of approximately 1 mg I/mL, which is equivalent to approximately 2 mg iohexol/ml (ppm).

This shows that Raman spectrometry is able to follow the concentration of iodinated X-ray media in water down to low ppm levels and that it can be used in on-line monitoring of rinse water and effluents following the cleaning of process equipment after termination of the process cycle.

What is claimed is:

1. A process for the production of an organic iodinated X-ray contrast agent, characterized in that process control comprises near-infrared or infrared vibrational spectroscopic monitoring of an aqueous or alcoholic reaction mixture in at least one of the process steps.

2. A process as claimed in claim 1 wherein said spectroscopic monitoring comprises near-infrared spectroscopic monitoring.

3. A process as claimed in claim 1 wherein said spectroscopic monitoring comprises infrared spectroscopic monitoring.

4. A process as claimed in claim 1 wherein said reaction mixture is aqueous.

5. A process as claimed in claim 4 wherein said reaction mixture is an aqueous solution.

6. A process as claimed in claim 1 wherein process parameters are adjusted following an automated comparison of data deriving from detected vibrational spectra with predetermined calibration data.

7. A process as claimed in claim 6 wherein said calibration data are derived from multivariate analysis of vibrational spectra of a set of calibration samples.

8. A process as claimed in claim 1 wherein said spectroscopic monitoring involves in-situ measurement of vibrational spectra in a reaction vessel or a duct connecting reaction vessels.

9. A process as claimed in claim 1 wherein said spectroscopic monitoring involves on-line sampling of said reaction mixture from a reaction vessel or a duct connecting reaction vessels and measurement of vibrational spectra of samples thus drawn from said vessel or duct.

10. A process as claimed in claim 1 wherein said vibrational spectroscopic monitoring involves monitoring physical characteristics of a solid product.

11. A process as claimed in claim 10 wherein said vibrational spectroscopic monitoring involves monitoring the crystalline type of a solid product.

12. A process as claimed in claim 1 wherein said X-ray contrast agent is a non-ionic X-ray contrast agent.

13. A process as claimed in claim 1 wherein said X-ray contrast agent is selected from iohexol, iopentol, iodixanol, iopamidol and ioversol.

14. A process as claimed in claim 1, wherein said reaction mixture includes $C_{1-4}$ alkanols and $C_{2-6}$ alkoxyalkanols.

15. A process as claimed in claim 9, wherein the alkoxy alcohol is 2-methoxyethanol.

* * * * *